US011280789B2

(12) United States Patent
Shen et al.

(10) Patent No.: US 11,280,789 B2
(45) Date of Patent: Mar. 22, 2022

(54) COMPOSITIONS, KITS, AND METHODS FOR CELL SEPARATION

(71) Applicant: REGENTS OF THE UNIVERSITY OF MINNESOTA, Minneapolis, MN (US)

(72) Inventors: Wei Shen, Roseville, MN (US); Mengen Zhang, St. Paul, MN (US); Bin Xu, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 140 days.

(21) Appl. No.: 15/491,233

(22) Filed: Apr. 19, 2017

(65) Prior Publication Data

US 2017/0299585 A1  Oct. 19, 2017

Related U.S. Application Data

(60) Provisional application No. 62/324,666, filed on Apr. 19, 2016.

(51) Int. Cl.
| | | |
|---|---|---|
| *G01N 33/543* | (2006.01) | |
| *G01N 33/569* | (2006.01) | |
| *A61K 38/16* | (2006.01) | |
| *C12Q 1/6841* | (2018.01) | |

(52) U.S. Cl.
CPC ..... *G01N 33/56966* (2013.01); *C12Q 1/6841* (2013.01)

(58) Field of Classification Search
CPC ............. G01N 33/56966; G01N 33/53; G01N 33/531; C12Q 1/6841; A61K 39/44; A61K 39/385; A61K 2039/625
See application file for complete search history.

(56) References Cited

FOREIGN PATENT DOCUMENTS

WO    WO 2013040007 A2    3/2013

OTHER PUBLICATIONS

Dong et al. A general strategy for isolation of endothelial cells from murine tissues. Arteriosclerosis, thrombosis, and vascular biology 1997, vol. 17, No. 8, pp. 1599-1604 (Year: 1997).*
Baganizi et al. A simple microfluidic platform for long-term analysis and continuous dual-imaging detection of T-cell secreted IFN-gamma and IL-2 on antibody-based biochip. Biosensors 2015, vol. 5, pp. 750-767. (Year: 2015).*
Aggarwal, "Human mesenchymal stem cells modulate allogeneic immune cell responses" 2005 *Blood*, 105:1815-1822.
Barkley, "Bubble-induced detachment of affinity-adsorbed erythrocytes" Oct. 2004 *Biotechnol Appl Biochem.*, 40(Part 2):145-149.
Bauer, "Advances in cell separation: Recent developments in counterflow centrifugal elutriation and continuous flow cell separation" Feb. 1999 *J Chromatogr B.*, 722(1-2):55-69.
BD Biosciences, "CD Marker Handbook" 2010.
Bell, "Models for specific adhesion of cells to cells" 1978 *Science*, 200:618-627.

(Continued)

*Primary Examiner* — Shafiqul Haq
(74) *Attorney, Agent, or Firm* — Mueting Raasch Group

(57) ABSTRACT

A cell-capturing substrate, methods of using the cell-capturing substrate that allow for label-free cell separation, and kits that incorporate the cell-capturing substrate.

11 Claims, 11 Drawing Sheets

Specification includes a Sequence Listing.

(56) References Cited

OTHER PUBLICATIONS

Bhagat, "Microfluidics for cell separation" 2010 *Med Biol Eng Comput.*, 48:999-1014.
Boldicke, "Anti-VEGFR-2 scFvs for cell isolation. single-chain antibodies recognizing the human vascular endothelial growth factor receptor-2 (VEGFR-2/flk-1) on the surface of primary endothelial cells and preselected. CD34(+) cells from cord blood" 2001 *Stem Cells*, 19:24-36.
Cao, "Detachment strategies for affinity-adsorbed cells" 2002 *Enzyme Microb Technol.*, 31:153-160.
Chan, "Label-free separation of human embryonic stem cells and their cardiac derivatives using raman spectroscopy" Feb. 2009 *Anal Chem.*, 81(4):1324-1331.
Chang, "A continuous size-dependent particle separator using a negative dielectrophoretic virtual pillar array" Nov. 2008 *Lab on a Chip*, 8(11):1930-1936.
Cheng, "A microfluidic device for practical label-free CD4+T cell counting of HIV-infected subjects" 2007 *Lab on a Chip*, 7:170-178.
Choi, "Continuous hydrophoretic separation and sizing of microparticles using slanted obstacles in a microchannel" 2007 *Lab on a Chip*, 7:890-897.
Dainiak, "Detachment of affinity-captured bioparticles by elastic deformation of a macroporous hydrogel" 2006 *Proc Natl Acad Sci U S A.*, 103:849-854.
David, "Magnetic cell sorting purification of differentiated embryonic stem cells stably expressing truncated human CD4 as surface marker" 2005 *Stem Cells*, 23:477-482.
Donaldson, "Separation by counterflow centrifugal elutriation and analysis of T- and B-lymphocytic cell lines in progressive stages of cell division cycle" 1997 *J Immunol Methods.*, 203:25-33.
Fu, "A microfabricated fluorescence-activated cell sorter" 1999 *Nat Biotechnol.*, 17:1109-1111.
Fujioka, "Difference in infrared spectra from cultured cells dependent on cell-harvesting method" 2003 *Appl Spectrosc.*, 57:241-243.
Furdui, "Immunomagnetic T cell capture from blood for PCR analysis using microfluidic systems" Dec. 2004 *Lab on a Chip*, 4(6):614-618.
Gawad, "Micromachined impedance spectroscopy flow cytometer for cell analysis and particle sizing" 2001 *Lab on a Chip*, 1:76-82.
Guo, "A new technique for the isolation and surface immobilization of mesenchymal stem cells from whole bone marrow using high-specific DNA aptamers" Oct. 2006 *Stem Cells*, 24(10):2220-2231.
Han, "Paramagnetic capture mode magnetophoretic microseparator for high efficiency blood cell separations" 2006 *Lab on a Chip*, 6:265-273.
Hedlund, "Selection of embryonic stem cell-derived enhanced green fluorescent protein-positive dopamine neurons using the tyrosine hydroxylase promoter is confounded by reporter gene expression in immature cell populations" May 2007 *Stem Cells*,25(5):1126-1135.
Heng, "Comparison of enzymatic and non-enzymatic means of dissociating adherent monolayers of mesenchymal stem cells" 2009 *Biol Proc Online*, 11:161-169.
Hu, "Marker-specific sorting of rare cells using dielectrophoresis" 2005 *Proc Natl Acad Sci U S A.*, 102:15757-15761.
Hubbell, "Endothelial cell-selective materials for tissue engineering in the vascular graft via a new receptor" 1991 *Bio-Technology*, 9:568-572.
Hubble, "Affinity cell separations: Problems and prospects" 1997 *Trends Biotechnol.*, 15:249-255.
Hubble, "Dissociation of multivalent antibody-antigen interactions" 1997 *Immunol Today*, 18:305-306.
Ibrahim, "High-speed cell sorting: Fundamentals and recent advances" 2003 *Curr Opin Biotechnol.*, 14:5-12.
Inglis, "Continuous microfluidic immunomagnetic cell separation" 2004 *Appl Phys Lett.*, 85:5093-5095.
Inglis, "Microfluidic high gradient magnetic cell separation" 2006 *J Appl Phys.*, 99:08K101.
Jones, "Isolation and characterization of bone marrow multipotential mesenchymal progenitor cells" 2002 *Arthritis Rheum.*, 46:3349-3360.
Jung, "Culture of human kidney proximal tubular cells—the effect of various detachment procedures on viability and degree of cell detachment" 1995 *Cellular Physiology and Biochemistry*, 5:353-360.
Kumar, "Affinity fractionation of lymphocytes using a monolithic cryogel" Dec. 2003 *J Immunol Methods*, 283:185-194.
Lewis, "Rare event selection of fetal nucleated erythrocytes in maternal blood by flow cytometry" 1996 *Cytometry*, 23:218-227.
Liu, "Dynamic presentation of immobilized ligands regulated through biomolecular recognition" 2010 *J Am Chem Soc.*, 132:13630-13632.
Mammen, "Polyvalent interactions in biological systems: Implications for design and use of multivalent ligands and inhibitors" 1998 *Angewandte Chemie-International Edition*, 37:2755-2794.
Mandrusov, "Membrane-based cell affinity-chromatography to retrieve viable cells" 1995 *Biotechnol Prog.*, 11:208-213.
Massia, "Vascular endothelial-cell adhesion and spreading promoted by the peptide redv of the iiics region of plasma fibronectin is mediated by integrin alpha-4-beta-1" 1992 *J Biol Chem.*, 267:14019-14026.
Miltenyi, "High-gradient magnetic cell-separation with macs" 1990 *Cytometry*, 11:231-238.
Miwa, "Adhesion-based cell sorter with antibody-coated amino-functionalized-parylene surface" 2008 *J Microelectromech Syst.*, 17:611-622.
Nagrath, "Isolation of rare circulating tumour cells in cancer patients by microchip technology" 2007 *Nature*, 450:1235-U10.
Nordon, "Design of hollow fiber modules for uniform shear elution affinity cell separation" 1997 *Artif Organs*, 21:107-115.
NSF "Award abstract #1134148: A Novel Cell Release Method for Affinity-based Cell Separation" Aug. 2011.
Papadaki, "Tissue engineering of functional cardiac muscle: Molecular, structural, and electrophysiological studies" 2001 *American Journal of Physiology—Heart and Circulatory Physiology*, 280:H168-H178.
Piner, "'Dip-pen'nanolithography" 1999 *Science*, 283:661-663.
Plouffe, "Controlled capture and release of cardiac fibroblasts using peptide-functionalized alginate gels in microfluidic channels" 2009 *Lab on a Chip*, 9:1507-1510.
Plouffe, "Peptide-mediated selective adhesion of smooth muscle and endothelial cells in microfluidic shear flow" 2007 *Langmuir*, 23:5050-5055.
Plouffe, "Microfluidic depletion of endothelial cells, smooth muscle cells, and fibroblasts from heterogeneous suspensions" 2008 *Lab on a Chip*, 8:462-472.
Putnam, "Cell affinity separations using magnetically stabilized fluidized beds—erythrocyte subpopulation fractionation utilizing a lectin-magnetite support" 2003 *Biotechnol Bioeng.*, 81:650-665.
Radisic, "Micro- and nanotechnology in cell separation" Mar. 2006 *International Journal of Nanomedicine*, 1(1):3-14.
Ryan, "Molecular crowding on the cell-surface" 1988 *Science*, 239:61-64.
Sharma, "Affinity chromatography of cells and cell-membranes" 1980 *J Chromatogr.*, 184:471-499.
Shen, "Tuning the erosion rate of artificial protein hydrogels through control of network topology" Feb. 2006 *Nature Materials*, 5(2):153-158.
Sin, "Enrichment using antibody-coated microfluidic chambers in shear flow: Model mixtures of human lymphocytes" 2005 *Biotechnol Bioeng.*, 91:816-826.
Sohn, "Capacitance cytometry: Measuring biological cells one by one" Sep. 2000 *Proc Natl Acad Sci U S A.*, 97(20):10687-10690.
Ujam, "Isolation of monocytes from human peripheral blood using immuno-affinity expanded-bed adsorption" Sep. 2003 *Biotechnol Bioeng.*, 83(5):554-566.
Voidman, "Electrical forces for microscale cell manipulation" 2006 *Annu Rev Biomed Eng.*, 8:425-454.
Wang, "Isolation and counting of multiple cell types using an affinity separation" 2007 *Anal Chim Acta*, 601:1-9.

(56) References Cited

OTHER PUBLICATIONS

Wang, "Open-tubular capillary cell affinity chromatography: Single and tandem blood cell separation" 2008 *Anal Chem.*, 80:2118-2124.
Wankhede, "Cell detachment model for an antibody-based microfluidic cancer screening system" 2006 *Biotechnol Prog.*, 22:1426-1433.
Yang, "Cell separation on microfabricated electrodes using dielectrophoretic/gravitational field flow fractionation" Mar. 1999 *Anal Chem.*, 71:911-918.
Yang, "Dielectric properties of human leukocyte subpopulations determined by electrorotation as a cell separation criterion" 1999 *Biophys J.* 76:3307-3314.
Yeo, "Electroactive monolayer substrates that selectively release adherent cells" Aug. 2001 *Chembiochem.*, 2:590-3.
Zhang, "Affinity-Based Cell Separation with Efficient Cell Release and Minimal Biochemical and Biophysical Perturbation" poster presentation Apr. 19-22, 2015.
Zhang, "Efficient Release of Affinity-Captured Cells Using Coiled-Coil-Based Molecular Triggers" Mar. 2017 Macromolecular Bioscience, 17(3):16 pages.
Zhao, "Isolation and initial application of a novel peptide that specifically recognizes the neural stem cells derived from rhesus monkey embryonic stem cells" Jul. 2010 *Journal of Biomolecular Screening*, 15(6):687-694.
Zheng, "Streamline-based microfluidic devices for erythrocytes and leukocytes separation" 2008 *J Microelectromech Syst.*, 17:1029-1038.
Zhu, "Catch and release cell sorting: Electrochemical desorption of T-cells from antibody-modified microelectrodes" 2008 *Colloids and Surfaces B-Biointerfaces*, 64:260-268.

\* cited by examiner

Released cells

COMPOSITIONS, KITS, AND METHODS FOR CELL SEPARATION

CROSS-REFERENCE TO RELATED APPLICATION

This application claims priority to U.S. Provisional Patent Application No. 62/324,666, filed Apr. 19, 2016, which is incorporated herein by reference.

GOVERNMENT FUNDING

This invention was made with government support under 1134148 awarded by the National Science Foundation The government has certain rights in the invention.

SEQUENCE LISTING

This application contains a Sequence Listing electronically submitted via EFS-Web to the United States Patent and Trademark Office as an ASCII text file entitled "11005410101SequenceList_ST25.txt" having a size of 4 kilobytes and created on Apr. 18, 2017. The information contained in the Sequence Listing is incorporated by reference herein.

BACKGROUND

Cell separation is essential in many clinical practices as well as in basic biological research and can be used in areas ranging from disease diagnosis and cell-based therapy to studies of stem cell biology. Although various methods have been developed, it remains a challenge to isolate target cells with high purity, high yield, and minimal biochemical and biophysical perturbation.

SUMMARY

This disclosure describes, in one aspect, a cell-capturing substrate that includes a substrate, an effector bound to the substrate, and a capture ligand bound to the substrate. The capture ligand is specific for a cell surface protein.

This disclosure describes, in another aspect, a method that includes providing a cell-capturing substrate that includes a substrate; an effector bound to the substrate; and a capture ligand bound to the substrate, wherein the capture ligand is specific for a cell surface protein; exposing the cell-capturing substrate to a cell comprising the cell surface protein for a time sufficient to permit the capture ligand to bind to the cell surface protein; and exposing the cell-capturing substrate to a molecular trigger, wherein the molecular trigger binds to the effector.

This disclosure describes, in a further aspect, a kit that includes a cell-capturing substrate that includes a substrate; an effector bound to the substrate; and a capture ligand bound to the substrate, wherein the capture ligand is specific for a cell surface protein; and a molecular trigger, wherein the molecular trigger binds to the effector.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains at least one drawing or photograph executed in color. Copies of this patent or patent application publication with color drawings or photographs will be provided by the Office upon request and payment of the necessary fee.

DETAILED DESCRIPTION OF ILLUSTRATIVE EMBODIMENTS

Figure 1:
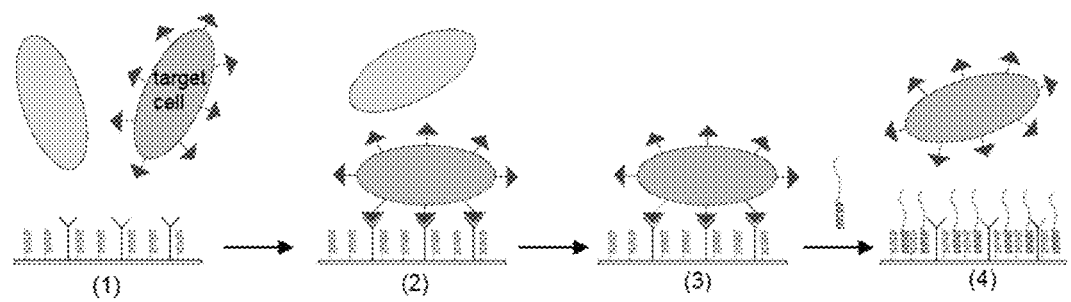
FIG. 1 shows a schematic of one embodiment of a method to separate cells. A mixture of cells is contacted with a capture substrate that includes a capture ligand, shown in (1). The capture ligand captures target cells, shown in (2). Non-target cells are washed away, shown in (3). The cell-releasing trigger is added, causing the release of the target cells from the capture ligand, shown in (4). Purple coil: Coiled-coil A; green coil: Coiled-coil B; yellow line: PEG; blue cell: target cell; yellow cell: non-target cell; Y: capture ligand; arrow: biomarker on target cell.

This disclosure describes a cell-capturing substrate, methods of using the cell-capturing substrate that allow for label-free cell separation, and kits that incorporate the cell-capturing substrate. The cell-capturing substrate includes a capture ligand and an effector bound to the substrate. The capture ligand specifically binds to a biomarker expressed by a type of cell or a population of cells. After the capture ligand binds to the cell, cells that do not bind to the capture ligand can be washed away. Adding a molecular trigger that binds to the effector can then be used to disrupt the interaction between the capture ligand and the cell, thereby releasing the cell from the substrate. The released cell can be collected.

Existing label-free methods for cell separation based on intrinsic physical characteristics of cells such as size, density, electrical properties, magnetic properties, and/or optical properties have insufficient specificity and resolution for many applications. For example, methods in which fluorescence, magnetic, or electrically polarizable tags are attached to cell surface biomarkers prior to isolation can be specific, but the tags need to be removed in some applications and both pre-isolation and post-isolation treatments can cause cell damage, cell loss, and/or undesired perturbation.

The cell separation described herein is mediated by the affinity between a cell surface biomarker and a complementary capture ligand immobilized on a separation matrix and is label-free, highly specific, and simple to operate. It can be difficult, however, to efficiently release affinity-captured cells in a viable and unperturbed state due to the multivalent nature of cell-material interactions, and this limitation is particularly relevant when rare, sensitive cells need to be isolated and used downstream in an unperturbed and functional state, such as in cell-based therapy and studies of stem cell biology. Various strategies have been used to detach affinity-captured cells such as, for example, breaking ligand-biomarker bonds through high shear force, elastic deformation of matrices, EDTA, or use of monovalent competitors at very high concentrations; non-specific cleavage of proteins by trypsin; use of an alginate gel as a separation matrix; or immobilizing capture ligands via bonds cleavable in response to electrical potentials. Each of these cell detachment methods have one or more drawbacks such as, for example, exposing cells to excessive biophysical perturbation and/or a harsh chemical environment that may cause cell damage and/or undesired responses (manifested as, for example, significantly reduced viability of mesenchymal stem cells after EDTA-based detachment); altering surface components of released cells (e.g., endogenous cell surface proteins cleaved and/or external capture ligands attached, which may elicit undesired stimulation and phenotype changes for sensitive cells); having insufficient detachment efficiency; and/or lacking the potential for general use.

The methods and compositions described in this disclosure address these challenges. In some embodiments, the present disclosure provides a novel platform that allows label-free, affinity-captured cells to be released efficiently with intact cell surface components in the absence of excessive biophysical perturbation and harsh chemical reagents.

In one aspect, this disclosure describes a cell-capturing substrate. The cell-capturing substrate includes a substrate, an effector bound to the substrate, and a capture ligand bound to the substrate.

In some embodiments, the substrate can include a tissue culture plate. In some embodiments, the substrate includes a chip, a biochip, a bead, a magnetic bead, a microarray, a microfluidic chamber, a microfluidic channel, and/or another high throughput solution.

The effector can include, for example, a protein, a nucleic acid molecule, or a small molecule. The effector is capable of binding to a molecular trigger. The effector and the molecular trigger can be a pair of heterodimerizable molecules that are capable of reversible, noncovalent self-assembly at an appropriate temperature for the assay being performed. Typically, appropriate temperatures reflect physiological temperatures. The effector and the molecular trigger can, in some embodiments self-assemble at temperatures of at least 20° C., at least 22° C., at least 24° C., at least 25° C., at least 27° C., at least 30° C., at least 35° C., at least 37° C., or at least 40° C., up to 42° C., or up to 45° C. As used herein, the term "self-assembly" refers generically to a property of two heterodimerizable molecules to noncovalently and reversibly assemble into a complex. The complex can be a dimeric complex. In the context of nucleic acid molecules, the term "self-assembly" is more typically referred to as hybridization. When the effector includes a protein, the protein can form a protein complex including, for example, a dimer, a heterodimer, a tetramer, etc. For example, the protein can include an alpha helix monomer. In some embodiments, the effector includes a protein that includes a first coiled-coil domain and the molecular trigger includes a protein that includes a second coiled coil domain. The first coiled coil domain and the second coiled coil domain can dimerize and/or form a super coil. In some embodiments, the effector and/or the molecular trigger include an amino acid sequence listed in Table 1.

TABLE 1

| CysA | MRGSHHHHHHGSDDDDKASSGSGCSGSGTSGDL ENEVAQLEREVRSLEDEAAELEQKVSRLKNEIE DLKAEIGDHVAPRDTSW (SEQ ID NO: 1) |
|---|---|
| Bcys | MRGSHHHHHHGSDDDDKWASGTSGDLKNKVAQL KRKVRSLKDKAAELKQEVSRLENEIEDLKAKIG DHVAPRDTSMGGC (SEQ ID NO: 2) |
| [A] | SGDLENEVAQLEREVRSLEDEAAELEQKVSRLK NEIEDLKAE (SEQ ID NO: 3) |
| [B] | SGDLKNKVAQLKRKVRSLKDKAAELKQEVSRLE NEIEDLKAK (SEQ ID NO: 4) |

In one exemplary embodiment, the effector can include [A] and the molecular trigger can include [B]. In another embodiment, the effector can include cysA and the molecular trigger can include Bcys. In another embodiment, the effector can include [B] and the molecular trigger can include [A]. In yet another embodiment, the effector can include Bcys and the molecular trigger can include cysA.

In some embodiments, the effector and/or the molecular trigger can include the heterodimerizable domains described in International Publication No. WO 2013/04007, which is incorporated herein by reference for its description of heterodimerizable domains.

In some embodiments, the effector can be a nucleic acid molecule and the molecular trigger can be a complementary nucleic acid molecule. In some embodiments, the effector can be streptavidin and the molecular trigger can be biotin, or the effector can be biotin and the molecular trigger can be streptavidin. In some embodiments, the effector can be an aptamer and the molecular trigger can be its target, or the effector can be the target of an aptamer and the molecular trigger can be the aptamer. In some embodiments, the effector and the trigger can be other coiled-coil heterodimers or other protein heterodimers.

The effector may be bound to and/or immobilized on the substrate via any suitable method. In some embodiments where, for example, the effector is a protein, the protein may be bound to the substrate via an amine reactive crosslinker. The crosslinker can include, for example, N-hydroxysuccinimide (NHS) or epoxy. In some embodiments, the protein may be bound to the substrate through a thiol-reactive crosslinker or via other chemical reactions including, for example, click chemistry. In certain embodiments, immobilizing and/or binding the effector to the substrate does not affect the effector's capacity to bind to the molecular trigger.

In some embodiments, the molecular trigger further includes a spacer component. The spacer component can be, for example, a hydrophilic polymer chain including, for example, a zwitterionic polymer chain, a polysaccharide, a poly(N-isopropylacrylamide), an elastin-like polypeptide, a polyvinyl alcohol, a poly(hydroxyethylmethacrylate), and/or a polyethylene glycol (PEG). In some embodiments, the spacer component can be a polyethylene glycol (PEG). The spacer can include a PEG having a molecular weight of at least 5 kDa, 10 kDa, at least 20 kDa, at least 30 kDa, or at least 40 kDa. In some embodiments, the PEG has a molecular weight of at least 30 kDa. The components of the molecular trigger including the spacer component may be covalently bound to each other. In some embodiments, the spacer component repels cells.

The capture ligand has affinity for a particular molecular target such as, for example, a cell surface protein. The capture ligand and the molecular target can have a $K_A$ of at least $10^4 M$ such as, for example, at least $10^5 M$, at least $10^6 M$, or at least $10^7 M$. In some embodiments, the capture ligand specifically binds to a target such as, for example, a cell surface protein expressed on the surface of a target cell—i.e., a cell to be captured and/or separated. As used herein, the term "specifically binds" refers to any level of differential binding of the capture ligand to the molecular target compared to binding of the capture ligand to a non-target molecule. For example, in some embodiments, the ratio of the binding affinity of the capture ligand for the target molecule compared to the binding affinity of the capture ligand for off-target cells can be at least 2:1 such as, for example, at least 3:1, at least 5:1, at least 10:1, at least 15:1, or at least 20:1.

In some embodiments, the capture ligand can include an antibody, an antibody fragment that specifically binds to the target, an aptamer that specifically binds to the target, or a non-antibody peptide that specifically binds to the target. In some embodiments, the capture ligand can include an antibody such as, for example, an anti-CD31 antibody, an anti-CD3 antibody, an anti-CD4 antibody, an anti-CD8 antibody, an anti-CD19 antibody, an anti-CD20 antibody, an anti-CD34 antibody, an anti-CD56 antibody, an anti-CD235a antibody, an anti-CD146 antibody, an anti-CD326 antibody, an anti-CD11c antibody, an anti-CD123 antibody, an anti-CD14 antibody, an anti-CD33 antibody, an anti-CD66b antibody, an anti-CD41 antibody, an anti-CD61 antibody, and/or an anti-CD62 antibody. In some embodiments, the capture ligand can include any CD marker such as, for example, those listed at bdbiosciences.com/documents/cd_marker_handbook.pdf.

The capture ligand may be bound to and/or immobilized on the substrate via any suitable method. In many embodiments, immobilizing the capture ligand to the substrate has little to effect on the ability of the capture ligand to bind a cell surface protein. In some embodiments, the capture ligand may be bound to the substrate via an amine reactive crosslinker. The crosslinker can include, for example, N-hydroxysuccinimide (NHS) or epoxy. In some embodiments, the capture ligand may be bound to the substrate via a chemical reaction, such as click chemistry.

The target to be captured by the capture ligand can include a biological cell, a biological particle, a natural organic particle, a natural inorganic particle, a man-made organic particle, and/or a man-made inorganic particle. When the target is a cell, the cell to be captured can express at least one cell surface protein that is specific to the target cell—at least among the population of cells in the collected sample. Any suitable cell surface protein may be used. For example, a human umbilical vein endothelial cell (HUVEC) can be identified by its cell surface expression of CD31 (also known as Platelet endothelial cell adhesion molecule (PECAM-1)). For example, when the target is a T cell, the cell surface protein may be CD3, CD4, and/or CD8; when the target is a B cell, the cell surface protein may be CD19 and/or CD20; when the target is a hematopoietic stem cell, the cell surface protein may be CD34; when the target is an NK cell, the cell surface protein may be CD56; when the target is an erythrocyte, the cell surface protein may be CD235a; when the target is an endothelial cell, the cell surface protein may be CD146; when the target is an epithelial cell, the cell surface protein may be CD326; when the target is a dendritic cell, the cell surface protein may be CD11c and/or CD123; when the target is a macrophage and/or monocyte, the cell surface protein may be CD14 and/or CD33; when the target is a granulocyte, the cell surface protein may be CD66b; when the target is a platelet, the cell surface protein may be CD41, CD61, and/or CD62; when the target is a circulating tumor cell, the cell surface protein may be epithelial cellular adhesion molecule (EpCAM), N-cadherin, CD44, CD24, CD133, and/or CD166; when the target is a neoantigen-specific or tumor-antigen-specific T cell, the cell surface protein may be CD8, CD134, CD137, CD 28, CD 25, CD 27, and/or programmed cell death 1 (PD-1); when the target is a T memory stem cell, the cell surface protein may be CD8, stem cell antigen 1 (SCA1), IL-2 receptor β-chain (IL-2Rβ), CD45RA, and/or CD62L.

In some embodiments, the cell may express a combination of cell surface proteins that may provide increased specificity for a particular cell type compared to using a single cell surface protein. In such embodiments, multiple capture ligands may be bound to the substrate or the cell may be serially bound to substrates including different capture ligands.

In one embodiment, shown in FIG. 1, the substrate includes a cell-capturing substrate and a coiled-coil-based cell-releasing molecular trigger. The cell-capturing substrate can be prepared by co-immobilizing a capture ligand and an effector. In the embodiment of FIG. 1, the capture ligand is an antibody and the effector includes a coiled-coil domain A (Table 1). Target cells can be captured by the immobilized antibody. Captured cells can be released by contacting the cell-capturing substrate with a molecular trigger. In the embodiment of FIG. 1, B-PEG is the molecular trigger and includes B (Table 1), another a coiled-coil domain that heterodimerizes with A, and polyethylene glycol (PEG). The B-PEG molecules can be immobilized on the substrate through AB heterodimerization. Without wishing to be bound by theory, it is believed that cell release is driven by the energy gain when a PEG chain adopts an extended conformation, breaking nearby multivalent ligand-biomarker bonds.

Example 3 describes an embodiment in which the substrate includes microfluidic channels. The microfluidic channels were modified to include an anti-CD31 antibody for the selective capture of HUVEC cells. Imaging of the samples revealed that HUVECs were selectively captured (FIG. 11, panel (b)) in the channels with the designed surface. In channels with the surface modified with only cysA (no anti-CD31 antibody), few cells adhered (FIG. 1, panel (c)). In channels with the unmodified surface, both cells adhered with no selectivity (FIG. 11($d$)).

Using the substrates and methods described herein, a cell can be released without being exposed to harsh chemical and physical conditions, increasing the likelihood and/or extent to which the released cell has intact biochemical components on the surface with neither non-endogenous molecules attached nor endogenous cell-surface molecules cleaved. Using antibodies as capture ligands and using a protein-molecular trigger interaction (e.g. AB heterodimerization) that is not directly involved in cell-substrate interactions as a cell releasing trigger makes the methods described herein versatile and readily adaptable for any cell type.

In another aspect, this disclosure describes a method that includes providing a target-capturing substrate—e.g., a cell-capturing substrate, exposing the target-capturing substrate to a sample comprising the target—e.g., a sample comprising cells that express a biomarker that specifically binds to the capture ligand, and exposing the target-capturing substrate to a molecular trigger.

The target-capturing substrate can be exposed to a sample comprising the target for an exposure time sufficient to permit the capture ligand to bind to the target. For example, the target-capturing substrate can be exposed to a sample comprising the target for a minimum exposure time of at least two minutes, at least five minutes, at least 10 minutes, at least 15 minutes, at least 20 minutes, at least 30 minutes, at least 40 minutes, at least 50 minutes, at least 60 minutes, or at least two hours. The target-capturing substrate can be exposed to a sample comprising the target for a maximum exposure time of no more than 24 hours such as, for example, no more than three hours, no more than two hours, no more than 60 minutes, no more than 50 minutes, no more than 40 minutes, no more than 30 minutes, no more than 20 minutes, no more than 15 minutes, or no more than 10 minutes. In some embodiments, the length of time that the target-capturing substrate is exposed to a sample comprising the target may be a range having endpoints defined by any minimum exposure time listed above and any maximum exposure time listed above that is greater than the minimum exposure time.

The sample comprising the target can further include non-target molecules and/or nontarget cells. For example, when a cell-capturing substrate is exposed to a cell comprising a particular cell surface protein, the cell-capturing substrate can simultaneously be exposed to at least one cell type that does not express the target cell surface protein. For example, the cell-capturing substrate may be exposed to a composition including two, three, four, five, or more types of cells in which fewer than all of the types of cells express the target cell surface protein.

The method can further include removing any non-target molecule or non-target—e.g., a cell that does not comprise the cell surface protein and/or a cell that does not bind to the capture ligand prior to exposing the cell-capturing substrate to the molecular trigger. A non-target molecule and/or non-target can be removed by, for example, washing the target-capturing substrate.

In some embodiments, the target-capturing substrate is exposed to a molecular trigger for a time sufficient to disrupt the interaction between the capture ligand and the target. For example, the target-capturing substrate can be exposed to the molecular trigger for a minimum release time of at least two minutes, at least five minutes, at least 10 minutes, at least 15 minutes, at least 20 minutes, at least 30 minutes, at least 40 minutes, at least 50 minutes, at least 60 minutes, or at least two hours. The target-capturing substrate can be exposed to a molecular trigger for a maximum release time of no more than 24 hours such as, for example, no more than three hours, no more than two hours, no more than 60 minutes, no more than 50 minutes, no more than 40 minutes, no more than 30 minutes, no more than 20 minutes, no more than 15 minutes, or no more than 10 minutes. In some embodiments, the length of time that the target-capturing substrate is exposed to a molecular trigger may be a range having endpoints defined by any minimum release time listed above and any maximum release time listed above that is greater than the minimum release time.

The method can further include collecting the target released from the target-capturing substrate as a result of contacting the target-capturing substrate with the molecular trigger. For example, a cell released from the target-capturing substrate can be collected by, for example, washing the target-capturing substrate and/or by collecting a liquid sample. In some embodiments, the collected target molecules and/or collected target cells may be centrifuged.

In certain embodiments, the methods described in this disclosure harness molecular recognition of self-assembling molecules, the conformational energy gain of extended PEG chains, and the use a molecular trigger to efficiently release affinity-captured cells without exposing cells to harsh physical and chemical conditions. A cell released using this method has completely intact biochemical components on the surface. In contrast, cells released using monovalent competitors as in previously reported cell separation methods have non-endogenous molecules (e.g., aptamers or sugar molecules) attached. In addition, monovalent competitor methods require both the capture ligand and the releasing agent be specifically designed for each type of target cells, which itself could be challenging and require a substantial amount of work. In contrast, the compositions and methods described in this disclosure can be readily adapted to many types of target cells, using existing or newly designed antibodies as capture ligands.

In some embodiments, the molecular trigger is B-PEG. B-PEG can act as universal cell-releasing molecular trigger because the molecular mechanisms underlying cell release, including both AB heterodimerization and adoption of extended conformations by PEG chains, are not directly involved in cell-substrate interactions. This cell detachment method, together with label-free and highly specific affinity capture, allows cell separation to be performed with unprecedented collective qualities in terms of high specificity, high yield, and minimal biochemical and biophysical perturbation on cells. The benefits are particularly relevant for isolating cells that must be used in an unperturbed, functional state or in applications where minimal perturbation of cells is important. For example, the methods and compositions described in this disclosure may be particularly useful for cell-based therapies and/or for studying stem cells.

In a further aspect, this disclosure provides kits that include the cell-capturing substrate and/or the molecular trigger.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1—Isolation of Human Umbilical Vein Endothelial Cells

This example describes an affinity-based cell capturing substrate that allows efficient release of captured cells with minimal biochemical and biophysical perturbation. An antibody for platelet endothelial cell adhesion molecule (PECAM-1) and a coiled-coil A are co-immobilized on a substrate. The substrate selectively captures PECAM-1 positive human umbilical vein endothelial cell (HUVECs) from a mixture of HUVECs and 3T3 fibroblasts; the capture efficiency and selectivity are 10,000 cells/cm$^2$ and 92%, respectively. Addition of B-PEG, where B is another coiled-coil that forms heterodimers with A and where PEG is poly(ethylene glycol), leads to efficient release of captured HUVECs in the absence of trypsin and large shear stress.

Figure 2:
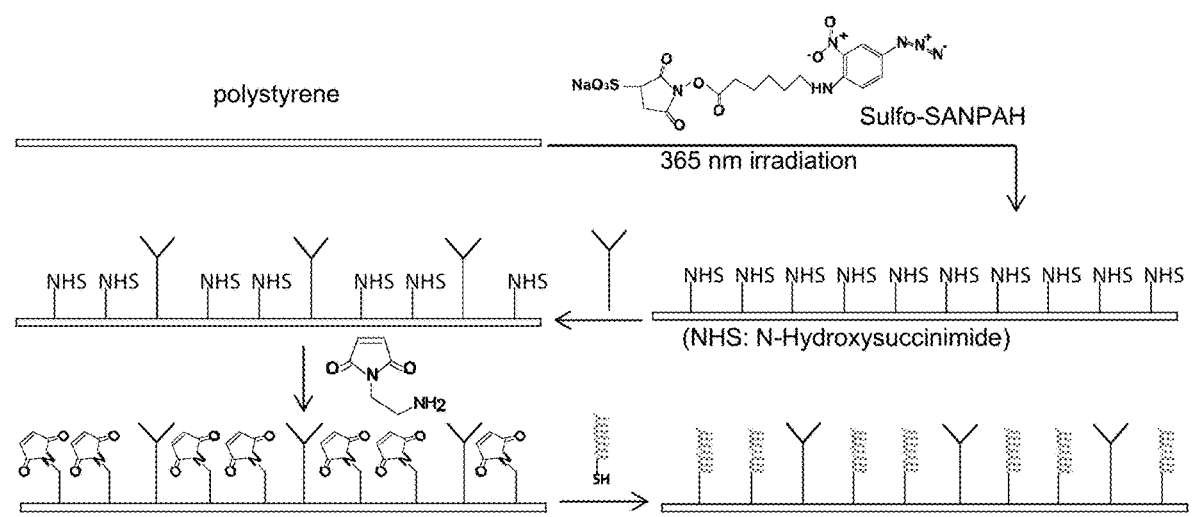
FIG. 2 shows a schematic of one embodiment of a method to prepare a functionalized substrate.
Figure 3:
FIG. 3 shows a schematic of one embodiment of a method to prepare a cell-releasing molecular trigger.
Figure 4:
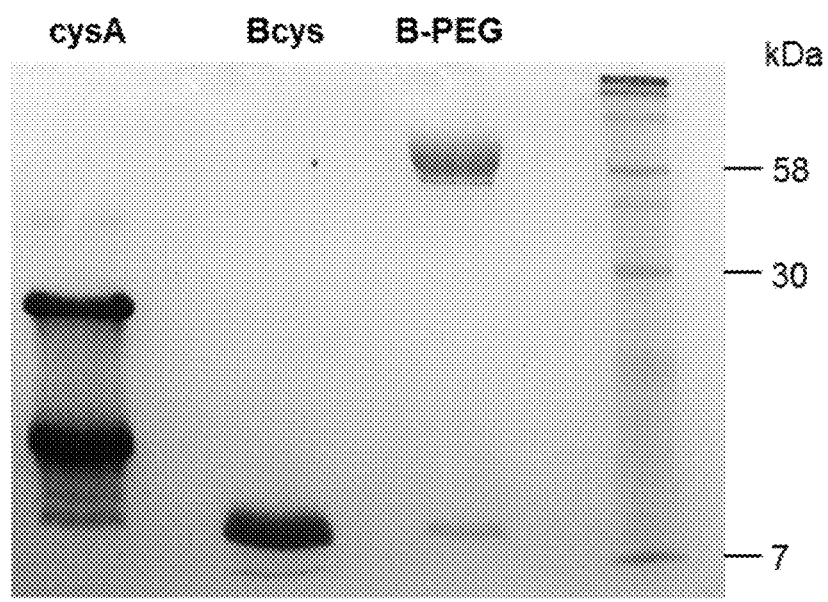
FIG. 4. SDS-PAGE of cysA (lane 1), Bcys (lane 2), and B-PEG (PEG: 30 kDa) (lane 3), confirming the protein expression, protein purification, and the conjugation between Bcys and PEG were successful.

Preparation of the capture substrate functionalized with a capture ligand and an effector including a coiled-coil A is illustrated in FIG. 2. The surface of polystyrene tissue culture plates was treated with 1 mg/ml N-Sulfosuccinimidyl-6-[4'-azido-2'-nitrophenylamino] hexanoate (sulfo-SANPAH) under UV irradiation (365 nm) for 20 min to introduce the N-hydroxysuccinimide (NHS) group. An anti-human CD31 antibody (20 μg/ml in PBS), which selectively interacts with HUVECs, was immobilized on the NHS-functionalized surface through the NETS-amine reaction for 30 minutes. After a rinse, the non-consumed NHS group on the substrate was allowed to react with the solution of N-(2-Aminoethyl) maleimide trifluoroacetate salt (30 mM in PBS) for four hours to introduce the maleimide group, which was further reacted with the polypeptide cysA (600 μM in PBS, containing 5 mM tris(2-carboxyethyl)phosphine (TCEP)) for 24 hours to immobilize cysA through the thiol-maleimide reaction. The procedure to prepare the cell releasing molecular trigger B-PEG is illustrated in FIG. 3. A solution including polypeptide Bcys (1.38 mM in 2 M urea, pH 7.4, containing 20 mM TCEP) was allowed to react with PEG-maleimide (30 kDa) at a molar ratio of 1:15 for two days, followed by removal of unreacted PEG-maleimide through Ni-NTA metal-affinity chromatography and removal of unreacted Bcys through the thiopropyl-sepharose 6B resin.

A cell mixture containing HUVECs (labeled with the green-fluorescent live cell tracker calcein AM) and fibroblasts (labeled with the orange-fluorescent live cell tracker Orange CMTMR), each at a density of 200,000 cells/ml, was prepared in EGM-2 basal medium. The cell mixture was seeded on a capture substrate functionalized with both anti-CD31 antibody and cysA (200 μl of the cell mixture for each well in 48-well plates), a capture substrate functionalized with cysA only (prepared following the procedure for functionalizing a plate with a capture ligand and cysA except that the antibody solution was replaced with PBS), or a polystyrene tissue culture plate. After seeding, the cell mixture was incubated for 40 minutes, followed by washing with PBS to remove non-adherent cells. Imaging of the substrate before and after washing (FIG. 5) revealed that the selectivity with which HUVECs were captured.

Figure 5:
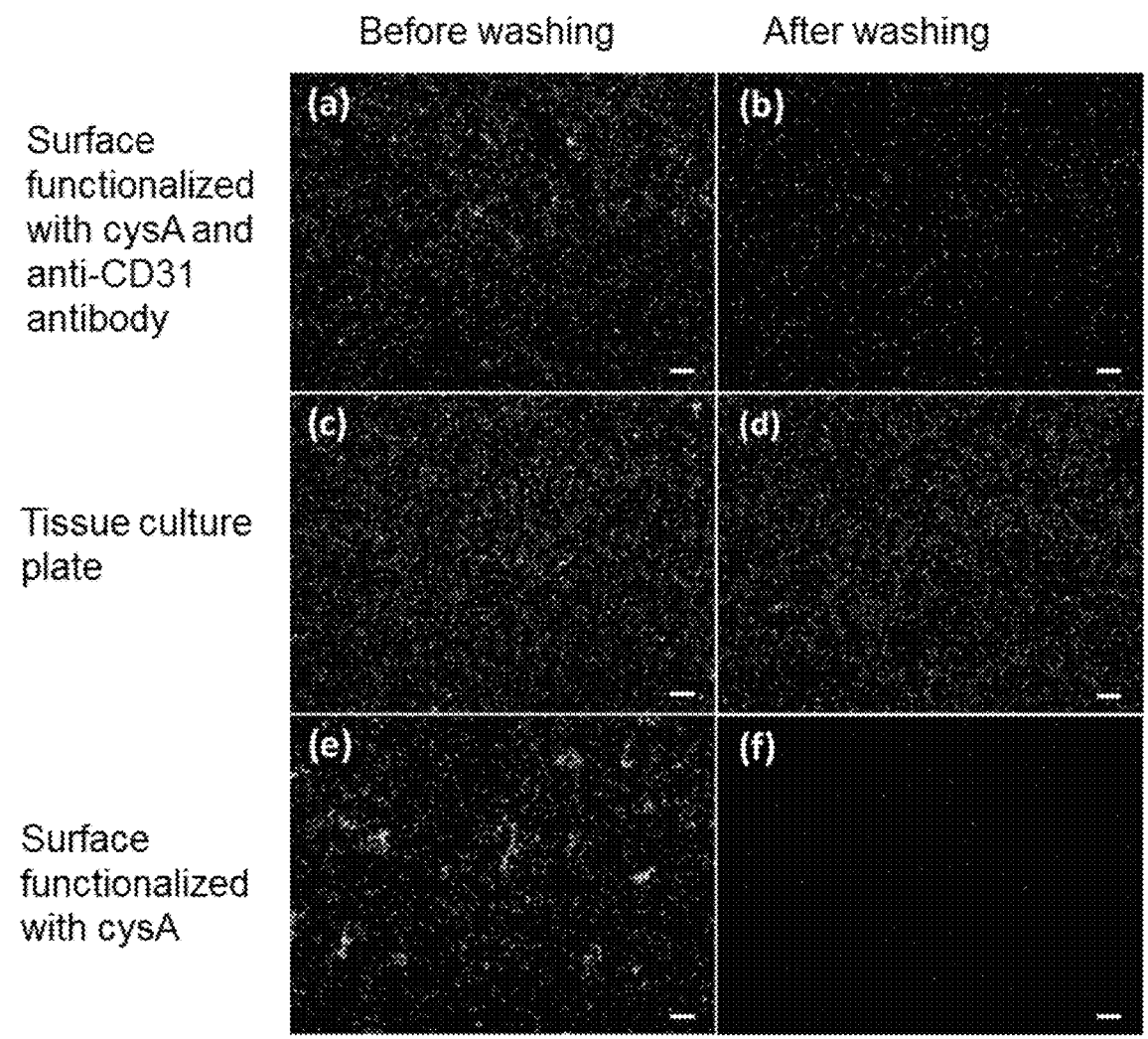
FIG. 5. Cell binding to a tissue culture plate, a substrate functionalized with cysA alone, or a substrate functionalized with cysA and anti-CD31 antibody. Human Umbilical Vein Endothelial Cells (HUVECs) (green) and 3T3 fibroblasts (orange) were mixed at 1:1 ratio and placed on the indicated surfaces at a density of 80,000 cells/cm$^2$. After 40 minutes of incubation, non-adherent cells were washed away. The scale bars are 500 µm. (a): surface functionalized with cysA and anti-CD31 antibody, before washing; (b) surface functionalized with cysA and anti-CD31 antibody, after washing; (c) tissue culture plate, before washing; (d) tissue culture plate, after washing; (e) surface functionalized with cysA, before washing; (f) surface functionalized with cysA, after washing.
Figure 6:
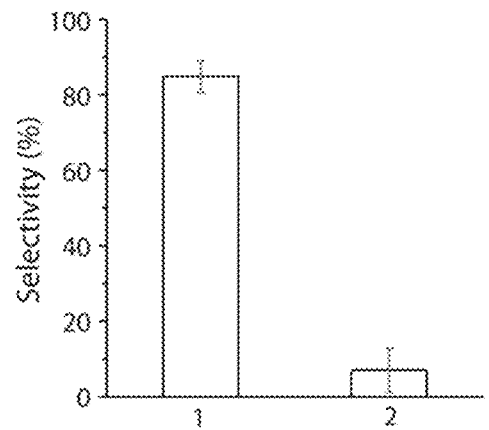
FIG. 6. Bar graph showing quantification of the selectivity of cell capture of HUVECs by a tissue culture plate (2) and a substrate functionalized with cysA and anti-CD31 antibody (1).

On the polystyrene tissue culture surface, after washing, both HUVECs and fibroblasts were captured; the selectivity of capturing HUVECs was close to 0 (FIG. 5, panel (d); FIG. 6). Selectivity was calculated as follows:

$$\text{selectivity} = \left(\frac{\text{captured target cells}}{\text{captured total cells}} - 0.5\right) 0.5$$

Figure 7:
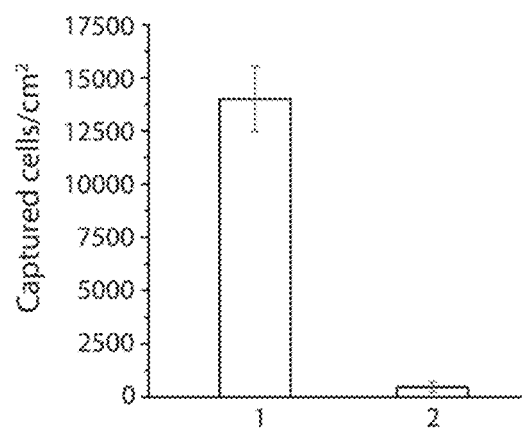
FIG. 7 shows capture capacity of a substrate functionalized with cysA and anti-CD31 antibody (1) and a substrate functionalized with cysA alone (2).

On the substrate functionalized with both anti-CD31 antibody and cysA, HUVECs were captured with a selectivity of 84.8±4.3% (FIG. 5, panel (b); FIG. 6). The cell capture capacity is 14009±1523 cells/cm$^2$ (FIG. 5, panel (b); FIG. 7). On the cysA-functionalized substrate, after washing, few cells of either type were captured (FIG. 5, panel (f); FIG. 7).

Figure 8:
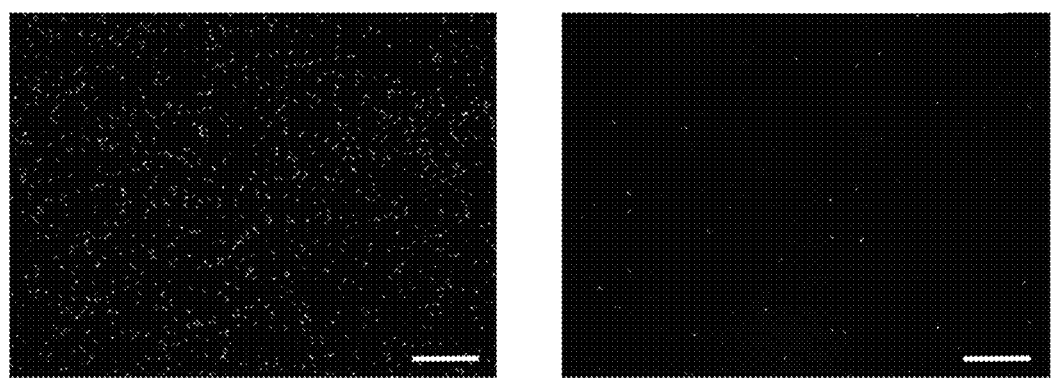
FIG. 8. HUVEC binding by a substrate functionalized with cysA and anti-CD31 antibody before (left) and after (right) adding B-PEG (30 kDa). The scale bars are 500 µm.
Figure 10:
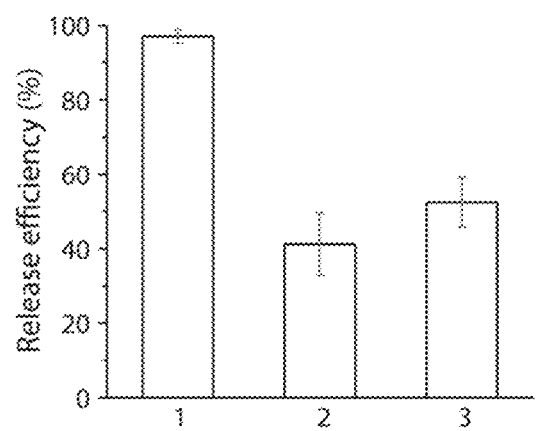
FIG. 10. Quantification of the release efficiency of HUVECs captured on the substrate functionalized with cysA and anti-CD31 antibody when B-PEG molecular triggers are added. (1) Release using B-PEG (30 kDa) for 30 minutes; (2) release using B-PEG (10 kDa) for 30 minutes; (3) release using B-PEG (10 kDa) for two hours.

To release the captured cells, the sample was incubated in 200 μl of EGM-2 basal medium containing 400 μM B-PEG for 30 minutes. Imaging of the HUVECs bound to a capture substrate functionalized with a capture ligand and polypeptide A before and after incubation with B-PEG revealed that the captured cells were released efficiently (97.1±1.8% of release) after 30 minutes of incubation (FIG. 8, FIG. 10). The HUVECs-containing liquid sample was collected in a tube and the substrate was washed with 200 μl of EGM-2 basal medium; the wash medium was also added to the tube.

Figure 9:
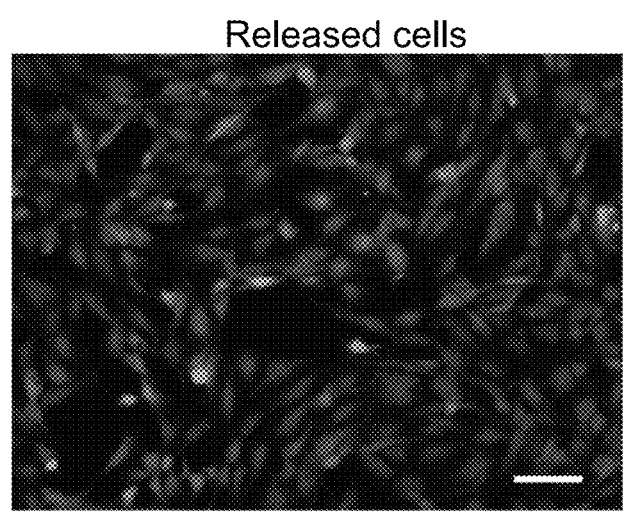
FIG. 9 shows that morphology of cells released from a substrate functionalized with cysA and anti-CD31 antibody by adding B-PEG and then cultured for four days on a tissue culture plate. Cells exhibited normal morphology and high viability. The scale bar is 100 µm.

The liquid sample was centrifuged, and the cells in the pellet were seeded in 96-well cell culture plates and cultured for four days. The resulting cells (shown in FIG. 9) exhibit similar attachment behavior, morphology, and viability as normally passaged HUVECs.

These results suggest that surface modification with a capture ligand and polypeptide A permits capture of HUVECs, as shown in FIG. 5, through the specific interaction between the immobilized antibody and the CD31 on the cell surface.

The specificity of cell release in response to A/B heterodimerization was confirmed in two other controls. Addition of B-PEG to a sample in which HUVECs were adhered to a polystyrene tissue culture surface, resulted in no cell detachment or cell death being observed, suggesting that B-PEG is not toxic to the cells and it does not trigger cell release when cells are captured on substrates having no immobilized cysA. Addition of PEG (30 kDa) to a sample in which HUVECs were adhered to a substrate functionalized with both anti-CD31 antibody and cysA, did not trigger cell detachment, suggesting that the B domain in B-PEG plays an essential role in releasing cells.

A/B heterodimerization and subsequent immobilization of B-PEG drives the cell release shown in FIG. 8.

Example 2—Effect of PEG Size on Cell Release Efficiency

The role of conformational energy gain of extended PEG chains in disrupting multivalent cell-substrate interactions can be demonstrated by observing the effect of the PEG size on cell release efficiency. When B-PEG (10 kDa) was used as a molecular trigger, cell release occurred much less efficiently than when B-PEG (30 kDa) was used as a molecular trigger, as shown in FIG. 10.

Example 3—Cell Separation in Microfluidic Channels

The channels of a polydimethylsiloxane device were modified with 3-glycidoxypropyltrimethoxysilane to first introduce an epoxy functional group, followed by immobilization of an antibody and $NH_2$-maleimide sequentially through the epoxy-amine reaction. The surface was further modified with cysA through a thiol-maleimide reaction. The dimensions of the channels were: 50 mm (length)×2 mm (width)×75 μm (height).

Anti-CD31 antibody was immobilized on the surface of the channels and a cell mixture containing red-fluorescent HUVECs and green-fluorescent OVCAR-3 cells at 1:1 ratio and 2 million cells/mL for each was used as a model system. The cell mixture was introduced into channels and incubated at 37° C. for 30 minutes, followed by removal of non-adherent cells with cell culture medium. The flow rate was controlled so that the adhered cells were exposed to the following shear stress: 0.5 dyn/cm$^2$ for four minutes, 1 dyn/cm$^2$ for two minutes, or 2 dyn/cm$^2$ for one minutes. The washing time was varied so that the total volume of liquid used for washing was the same in each case.

Figure 11:
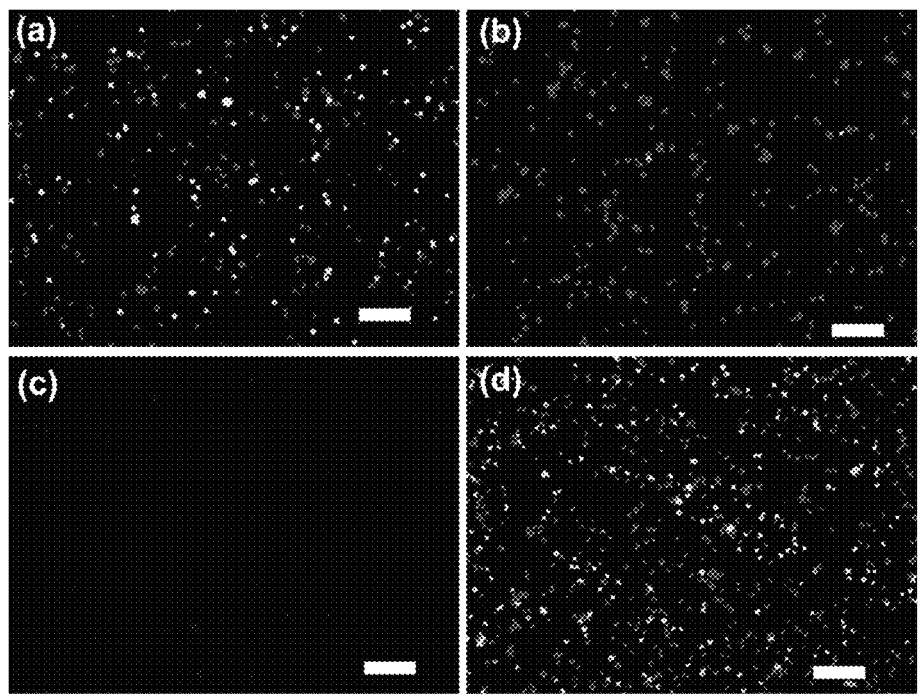
FIG. 11. Capture of HUVECs (red) from a mixture of HUVECs and OVCAR-3 cells (green), mixed at 1:1. (a) The mixture was seeded in a channel functionalized with the anti-CD31 antibody and the coiled-coil A. (b) Washing the sample described in (a) with a shear stress of 0.5 dyn/cm² for four minutes revealed selective capture of HUVECs. (c) In a control channel functionalized with A alone, few cells of either type adhered. (d) In a control channel with the unmodified surface, both cell types adhered with no selectivity, as revealed after washing. The scale bars are 200 µm.
Figure 12:
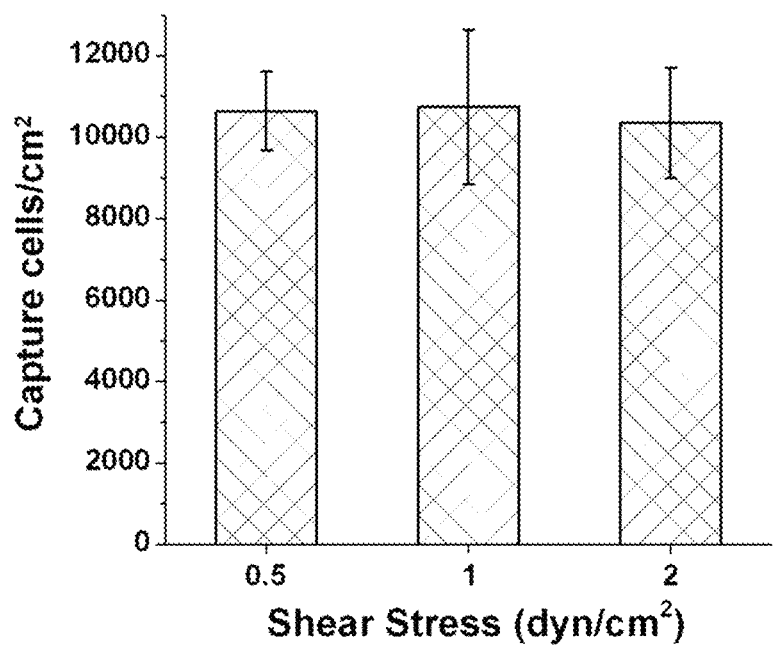
FIG. 12. Bar graph showing capture capacity at different shear stresses (n=3).
Figure 13:
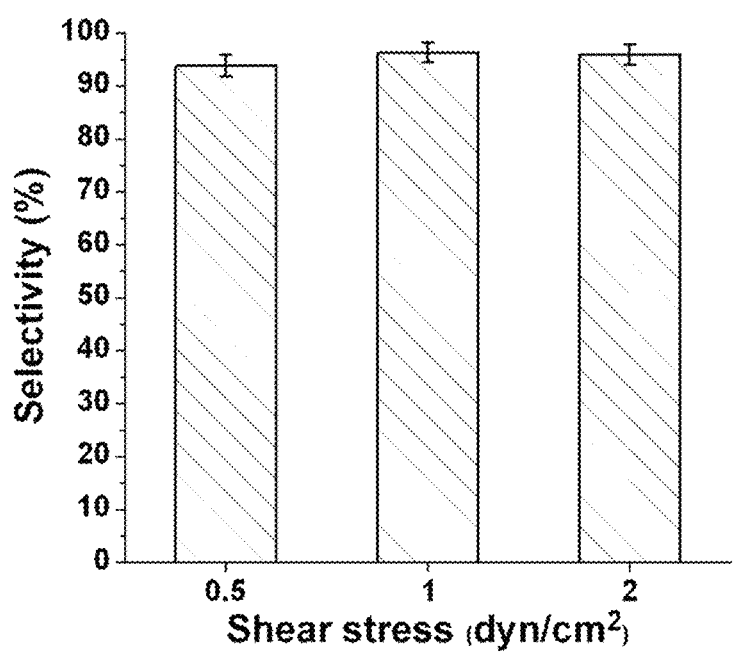
FIG. 13. Bar graph showing capture selectivity at different shear stresses (n=4).

Imaging of the samples revealed that HUVECs were selectively captured (FIG. 11, compare (a) and (b)) in the channels with the designed surface. In channels with the surface modified with only cysA (no anti-CD31 antibody), few cells adhered (FIG. 11(c)). In channels with the unmodified surface, both cells adhered with no selectivity (FIG. 11 (d)). For the channels with the designed surface, the capacity to capture HUVECs is 10637±961 cells/cm$^2$ when washed at a shear stress of 0.5 dyn/cm$^2$, 10735±1897 cells/cm$^2$ when washed at a shear stress of 1.0 dyn/cm$^2$, and 10345±1353 cells/cm$^2$ when washed at a shear stress of 2.0 dyn/cm$^2$ (FIG. 12). The capture selectivity is 93.9%±2.1% when washed at a shear stress of 0.5 dyn/cm$^2$, 96.3%±1.8% when washed at a shear stress of 1.0 dyn/cm$^2$, and 95.9%±1.9% when washed at a shear stress of 2.0 dyn/cm$^2$ (FIG. 13). Selectivity is defined as the ratio of targeted cells to the total cells captured on the surface.

Figure 14:
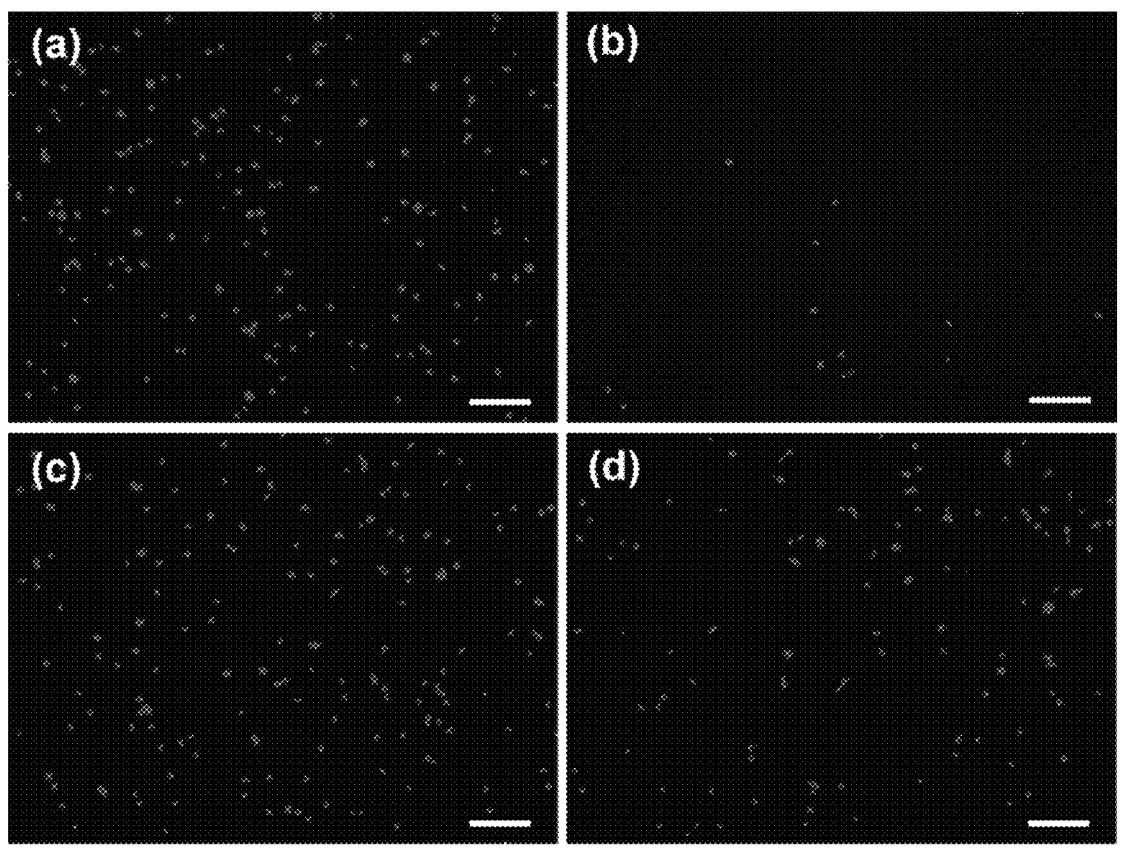
FIG. 14. Release of captured cells using B-PEG. (a) Captured HUVECs. (b) The captured HUVECs in (a) were efficiently released by 400 µM B-PEG. (c) Captured HUVECs. (d) The captured HUVECs in (c) were not efficiently released by 400 µM PEG (d). The scale bars are 200 µm.
Figure 15:
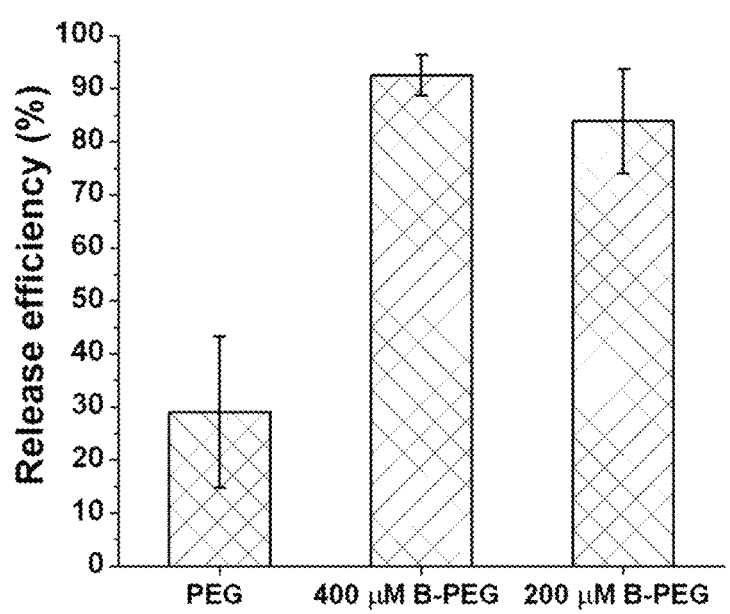
FIG. 15. Bar graph showing the release efficiency of captured cells with B-PEG and PEG solutions (n=3).

To release captured cells, a B-PEG solution (400 μM or 200 μM) or a PEG solution (400 μM) as a control was pumped into the channel with the flow rate controlled to expose cells to 1 dyn/cm$^2$. Release with B-PEG (400 μM) or PEG was conducted for 10 minutes; release with B-PEG (200 μM) was conducted for 20 minutes. The size of PEG is 30 kDa for all the molecules (PEG or B-PEG). The B-PEG solution efficiently released cells (FIG. 14, compare (a) and (b)), whereas the PEG solution did not (FIG. 14, compare (c) and (d)). Quantitative analysis revealed that the release efficiency is 92.5%±3.8% for 400 μM B-PEG and 83.8%±9.8% for 200 μM B-PEG (FIG. 15). The release efficiency with the PEG solution (control) is 28.9%±14.3% (FIG. 15).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A cell separation substrate comprising:
   a substrate;
   a capture antibody bound to the substrate, wherein the capture antibody is selected to bind to a target cell by binding to a cell surface protein expressed by the target cell;
   an effector bound to the substrate, the effector comprising a protein comprising a coiled coil domain; and
   a molecular trigger comprising:
      a protein comprising a coiled coil domain that forms a heterodimeric complex with the coiled coil domain of the effector, and
      a domain comprising a hydrophilic polymer chain having a molecular weight of at least 5 kDa;
   wherein the effector is bound to the substrate in proximity to the capture antibody so that the heterodimer complex disrupts binding between the capture antibody and the target cell.

2. The cell separation substrate of claim 1 wherein the substrate comprises a tissue culture plate.

3. The cell separation substrate of claim 1 wherein the substrate comprises a chip, a biochip, a bead, a magnetic bead, a microarray, a microfluidic channel, or a microfluidic chamber.

4. The cell separation substrate of claim 1 wherein the capture antibody comprises an antibody or an antibody fragment.

5. The cell separation substrate of claim 1 wherein the capture antibody comprises an anti-CD31 antibody, an anti-CD3 antibody, an anti-CD4 antibody, an anti-CD8 antibody, an anti-CD19 antibody, an anti-CD20 antibody, an anti-CD34 antibody, an anti-CD56 antibody, an anti-CD235a antibody, an anti-CD146 antibody, an anti-CD326 antibody, an anti-CD11 c antibody, an anti-CD123 antibody, an anti-CD14 antibody, an anti-CD33 antibody, an anti-CD66b antibody, an anti-CD41 antibody, an anti-CD61 antibody, an anti-CD62, an anti-EpCAM antibody, an anti-N-cadherin antibody, an anti-CD44 antibody, an anti-CD24 antibody, an anti-CD133 antibody, an anti-CD166 antibody, an anti-CD134 antibody, an anti-CD137 antibody, an anti-CD28 antibody, an anti-CD25 antibody, an anti-CD27 antibody, an anti-PD-1 antibody, an anti-SCA1 antibody, an anti-IL-2Rβ antibody, an anti-CD45RA antibody, an anti-CD62L antibody, or a mixture thereof.

6. The cell separation substrate of claim 1 wherein the heterodimerizable complex comprises a reversible, noncovalent complex comprising self-assembly of the effector and the molecular trigger.

7. The cell separation substrate of claim 1, wherein the effector comprises SEQ ID NO: 1.

8. The cell separation substrate of claim 1, wherein the molecular trigger comprises SEQ ID NO:2.

9. A cell-capturing substrate comprising:
   a substrate;
   a capture antibody bound to the substrate, the capture antibody being selected to bind to a target cell by binding to a cell surface protein expressed by the target cell;
   a target cell bound to the capture antibody;
   an effector bound to the substrate, the effector comprising a protein comprising a coiled coil domain; and
   a molecular trigger comprising:
      a protein comprising a coiled coil domain that forms a heterodimeric complex with the coiled coil of the effector, and
      a domain comprising a hydrophilic polymer chain having a molecular weight of at least 5 kDa;
   wherein the effector is bound to the substrate in proximity to the capture antibody so that the heterodimer complex disrupts binding between the capture antibody and the target cell.

10. The cell separation substrate of claim 1, wherein the hydrophilic polymer chain of the molecular trigger has a molecular weight of at least 10 kDa.

11. The cell-capturing substrate of claim 9, wherein the hydrophilic polymer chain of the molecular trigger has a molecular weight of at least 10 kDa.

* * * * *

SEQUENCE LISTING

<160> NUMBER OF SEQ ID NOS: 4

<210> SEQ ID NO 1
<211> LENGTH: 89
<212> TYPE: PRT
<213> ORGANISM: artificial
<220> FEATURE:
<223> OTHER INFORMATION: Polypeptide

<400> SEQUENCE: 1

Met Arg Gly Ser His His His His His Gly Ser Asp Asp Asp Asp
1               5                   10                  15

Lys Ala Ser Ser Gly Ser Gly Cys Ser Gly Ser Gly Thr Ser Gly Asp
                20                  25                  30

Leu Glu Asn Glu Val Ala Gln Leu Glu Arg Glu Val Arg Ser Leu Glu
            35                  40                  45

Asp Glu Ala Ala Glu Leu Glu Gln Lys Val Ser Arg Leu Lys Asn Glu
        50                  55                  60

Ile Glu Asp Leu Lys Ala Glu Ile Gly Asp His Val Ala Pro Arg Asp
65                  70                  75                  80

Thr Ser Trp Ser Glu Gln Ile Asp Asn
                85

<210> SEQ ID NO 2
<211> LENGTH: 85
<212> TYPE: PRT
<213> ORGANISM: artificial
<220> FEATURE:
<223> OTHER INFORMATION: Polypeptide

<400> SEQUENCE: 2

Met Arg Gly Ser His His His His His Gly Ser Asp Asp Asp Asp
1               5                   10                  15

Lys Trp Ala Ser Gly Thr Ser Gly Asp Leu Lys Asn Lys Val Ala Gln
                20                  25                  30

Leu Lys Arg Lys Val Arg Ser Leu Lys Asp Lys Ala Ala Glu Leu Lys
            35                  40                  45

Gln Glu Val Ser Arg Leu Glu Asn Glu Ile Glu Asp Leu Lys Ala Lys
        50                  55                  60

Ile Gly Asp His Val Ala Pro Arg Asp Thr Ser Met Gly Gly Cys Ser
65                  70                  75                  80

Glu Gln Ile Asp Asn
                85

<210> SEQ ID NO 3
<211> LENGTH: 48
<212> TYPE: PRT
<213> ORGANISM: artificial
<220> FEATURE:
<223> OTHER INFORMATION: Polypeptide

<400> SEQUENCE: 3

Ser Gly Asp Leu Glu Asn Glu Val Ala Gln Leu Glu Arg Glu Val Arg
1               5                   10                  15

Ser Leu Glu Asp Glu Ala Ala Glu Leu Glu Gln Lys Val Ser Arg Leu
                20                  25                  30

Lys Asn Glu Ile Glu Asp Leu Lys Ala Glu Ser Glu Gln Ile Asp Asn
            35                  40                  45

<210> SEQ ID NO 4

```
<211> LENGTH: 42
<212> TYPE: PRT
<213> ORGANISM: artificial
<220> FEATURE:
<223> OTHER INFORMATION: Polypeptide

<400> SEQUENCE: 4

Ser Gly Asp Leu Lys Asn Lys Val Ala Gln Leu Lys Arg Lys Val Arg
1               5                   10                  15

Ser Leu Lys Asp Lys Ala Ala Glu Leu Lys Gln Glu Val Ser Arg Leu
            20                  25                  30

Glu Asn Glu Ile Glu Asp Leu Lys Ala Lys
            35                  40
```